(12) United States Patent
Jarsch et al.

(10) Patent No.: US 9,221,909 B2
(45) Date of Patent: Dec. 29, 2015

(54) ANTIBODIES AGAINST HUMAN EPO RECEPTOR

(75) Inventors: Michael Jarsch, Bad Heilbrunn (DE); Manfred Kubbies, Penzberg (DE); Olaf Mundigl, Weilheim (DE); Nora Torres-Nagel, Habach (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1042 days.

(21) Appl. No.: 13/144,671

(22) PCT Filed: Jan. 13, 2010

(86) PCT No.: PCT/EP2010/000130
§ 371 (c)(1),
(2), (4) Date: Jul. 14, 2011

(87) PCT Pub. No.: WO2010/081679
PCT Pub. Date: Jul. 22, 2010

(65) Prior Publication Data
US 2012/0122120 A1 May 17, 2012

(30) Foreign Application Priority Data
Jan. 15, 2009 (EP) .................................... 09000499

(51) Int. Cl.
*C07K 16/00* (2006.01)
*C07K 16/28* (2006.01)
*C07K 16/44* (2006.01)

(52) U.S. Cl.
CPC ............. *C07K 16/2863* (2013.01); *C07K 16/44* (2013.01); *C07K 2317/34* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 6,998,124 | B1 | 2/2006 | Erickson-Miller et al. |
| 7,053,184 | B2 | 5/2006 | Lee |
| 7,081,523 | B2 | 7/2006 | Elliott |
| 2002/0031806 | A1 | 3/2002 | Lee |
| 2003/0215444 | A1 | 11/2003 | Elliott |
| 2004/0058393 | A1 | 3/2004 | Fukishima et al. |
| 2004/0071694 | A1 | 4/2004 | DeVries et al. |
| 2004/0175379 | A1 | 9/2004 | DeVries et al. |
| 2005/0227289 | A1 | 10/2005 | Reilly et al. |
| 2005/0244409 | A1 | 11/2005 | Erickson-Miller et al. |
| 2006/0018902 | A1 | 1/2006 | Reilly et al. |

FOREIGN PATENT DOCUMENTS

| | | |
|---|---|---|
| EP | 0 773 962 | 5/1997 |
| EP | 0776370 | 6/1997 |
| EP | 1 146 056 | 10/2001 |
| EP | 1 327 681 | 7/2003 |
| JP | 2003-310276 | 11/2003 |
| JP | 2005-89354 | 4/2005 |
| JP | 2005-531293 | 10/2005 |
| WO | 95/05469 | 2/1995 |
| WO | 96/03438 | 2/1996 |
| WO | 00/61637 | 10/2000 |
| WO | 03/073821 | 9/2003 |
| WO | 2004/035603 | 4/2004 |
| WO | 2005/100403 | 10/2005 |

OTHER PUBLICATIONS

Sytkowski AJ (Erythropoietin: Receptor Biology and Signal Transduction, 2004 Wiley, "http://www3.interscience.wiley.com/cgi-bin/booktext/109869817/BOOKPDFSTART"; retrieved from the Internet Mar. 5, 2009).*
Sytkowski AJ (Erythropoietin: Receptor Biology and Signal Transduction, 2004 Wiley, cited on IDS filed Aug. 19, 2011).*
Anonymous, EpoR Phospho (pY485 Rabbit Monoclonal Antibody Product Data Sheet, Epitomics, Inc. retrieved from the internet, Other Database, Mar. 23, 2009.
Anonymous, p-EpoR (Tyr456)-R.sc-20236-R, Santa Cruz Biotechnology Inc.,retrieved from the internet, Other Database, Jan. 5, 2008.
Arai, A., et al., "CrkL is Recruited through Its SH2 Domain to the Erythropoietin Receptor and Plays a Role in Lyn-mediated Receptor Signaling" The Journal of Biological Chemistry 276(35):33282-33290 (Aug. 31, 2001).
Barber, Dwayne L. et al., "A Common Epitope is Shared by Activated Signal Transducer and Activator of Transcription-5 (STAT5) and the Phosphorylated Erythropoietin Receptor: Implications for the Docking Model of STAT Activation" Blood 97(8):2230 (Apr. 15, 2001).
Barnes et al., "Advances in animal cell recombinant protein production: GS-NS0 expression system" Cytotechnology 32(2):109-23 (Feb. 2000).
Barnes et al., "Characterization of the stability of recombinant preotein production in the GS-NS0 expression system" Biotechnol Bioeng. 73(4):261-70 (May 2001).
Bergelson, Svetlana, et al., "Tyrosine residues within the intracellular domain of the erythropoietin receptor mediate activation of AP-1 transcription factors" The Jounal of Biological Chemistry 273(4):2396-2401 (Jan. 23, 1998).
Carter et al., "Humanization of an Anti-p185\\\superscript:HER2\\\ Antibody For Human Cancer Therapy" Proc Natl Acad Sci U S A. 89(10):4285-4289 (May 1992).
Damen, Jacqueline E., et al., "Phosphorylation of tyrosine 503 in the erythropoietin receptor (EpR) is essential for binding the P85 subunit of phosphatidylinositol (PI) 3-kinase and for EpR-associated PI 3-kinase activity" The Journal of Biological Chemistry 270(40):23402-23408 (Oct. 6, 1995).
D'Andrea, D., et al., "Anti-Erythropoietin Receptor (EPO-R) Monoclonal Anitbodies Inhibit Erythropoietin Binding and Neutralize Bioactivity" Blood 82(1):46-52 (Jul. 1993).

(Continued)

*Primary Examiner* — Laura B Goddard
*Assistant Examiner* — Meera Natarajan
(74) *Attorney, Agent, or Firm* — Grant Kalinowski

(57) ABSTRACT

An antibody binding to human EPO-R, characterized in specifically binding pY461, pY430 or p465 is useful for the determination of activated EPO receptor.

11 Claims, 2 Drawing Sheets

(56) References Cited

OTHER PUBLICATIONS

Duroecher et al., "High-level and high-throughput recombinant protein production by transient transfection of suspension-growing human 293-EBNA1 cells" Nucleic Acids Research 30(2):E9 (2002).
Elliot, S., et al., "Enti-Epo Receptor Anitbodies do not Predict Epo Receptor Expression" Blood 107:1892-1895 (2006).
Geisse et al., "Eurkaryotic Expression Systems: A Comparison" Protein Expression and Purification 8:271-282 (1996).
Grimmler, M., et al., "Cdk-Inhibitory Actvity and Stability of P27Kip1 are Directly Regulated by Oncogenic Tyrosine Kinases" Cell 128:369-280 (Jan. 26, 2007).
Hörtner M., et al., "A new high affinity binding site for suppressor of cytokine signaling-3 on the erythropoietin receptor" Eur. J. Biochem 269:2516-2526 (2002).
Huston et al. et al., "Protein engineering of single-chain Fv analogs and fusion proteins" Method Enzymol 203:46-88 (1991).
Jelkmann, W., et al., "The Erythropoietin Receptor in Normal and Cancer Tissues" Critical Reviews in Oncology Hematology 67:39-61 (2008).
Johnson et al., "Kabat Database and its applications: 30 years after the first variability plot" Nucleic Acids Research 28(1):214-218 (2000).
Jones, S., et al., "Human Erythropoietin Receptor: Cloning, Expression and Biological Characterization" Blood 76:31-35 (1990).
Kaufman, "Overview pf Vector Design for Mammalian Gene Expression" Molecular Biotechnology 16:151-160 (2000).
Kirkeby, A., et al., "Functional and Immunochemical Characterisation of Different Antobodies Against the Erythropoietin Receptor" Journal of Neuroscience Methods 164:50-58 (2007).
Li, Ke, et al., "Roles for an Epo Receptor Tyr-343 Stat5 Pathway in Proliferative Co-signaling with Kit" The Journal of Biological Chemistry 278(42):40702-40709 (Sep. 17, 2003).
Malkrides, S.C., "Components of Vectors for Gene Transfer and Expression in Mammalian Cells" Protein Expression and Purification 17:183-202 (1999).
Matthews, David J., et al., "A sequential dimerization mechanism for erythropoietin receptor activation" Proc. Nat. Acad. Sci. 93:9471-9476 (Sep. 1996).
Miller, Barbara, A., et al., "Identification of the erythropoietin receptor domain required for calcium channel activation" The Journal of Biological Chemistry 274(29):20465-20472 (Jul. 16, 1999).
Miura, O., et al., "Dimer- and Oligomerization of the Erythropoietin Receptor by Disulfide Bond Formation and Significance of the Region near the WSXWS Motif in Intracellular Transport" Archives of Biochemistry & Biophysics 306(1):200-208 (Oct. 1993).

Neuberger et al., "A hapten-specific chimaeric IgE antibody with human physiological effector function" Nature 314:268-270 (Mar. 21, 1985).
Norderhaug et al., "Versatile Vectors for Transient and Stable Expression of Recombinant Anitbody Molecules in Mammalian Cells" Journal of Immunological Methods 204:77-87 (1997).
Orlandi et al., "Cloning Immunoglobin Variable Domains for Expression by the Polymerase Chain Reaction" Proc. Natl. Acad. Sci. USA 86:3833-3837 (May 1989).
Queen et al., "A humanized antibody that binds to the interleukin 2 receptor" Proc. Natl. Acad. Sci. USA 86(24):10029-10033 (Dec. 1989).
Riechmann et al., "Reshaping human anitbodies for therapy" Nature 332(6162):323-327 (Mar. 24, 1988).
Schlaeger et al., "Transient Gene Expression in Mammalian Cells Grown in Serum-free Suspension Culture" Cytotechnology 30:71-83 (1999).
Schlaeger, "The Protein Hydrolysate, Primatone RL, is a Cost-effective Multiple Growth Promoter of Mammalian Cell Culture in Serum-containing and Serum-free Media and Displays Anti-apoptosis Properties" Journal of Immunological Methods 194:191-199 (1996).
Sytkowski, A.J., "Receptor Biology and Signal Transduction" Erythropoietin, [online], Wiley-VCH Verlag GmbH:73-100 (2004).
Werner et al., "Appropriate mammalian expression systems for biopharmaceuticals" Arzneimittel-Forschung (Drug Res.) 48(8):870-880 (1998).
Winkelmann, JC, et al., "The Gene for the Human Erythropoietin Receptor: Analysis of the Coding Sequence and Assignment to Chromosome 19p" Blood 76:24-30 (1990).
Wu, Hong, et al., "Functional interaction of erythropoietin and stem cell factor receptors is essential for erythroid colony formation" Proc. Natl. Acad. Sci. 94:1806-1810 (Mar. 1997).
Enzyme Immunoassay "Measurement Sensitivity" (English Translation), Eiji Ishikawa, et al., 2nd Edition, Igaku Shoin,:50-52 (Dec. 15, 1982).
Enzyme Immunoassay "Measurement Sensitivity" Eiji Ishikawa, et al., 2nd Edition, Igaku Shoin,:50-52 (Dec. 15, 1982).
Foote et al., "Antibody Framework Residues Affecting the Confirmation of the Hypervariable Loops" J Mol Biol 224:487-499 (1992).
Winter et al., "Antibody-Based Therapy—Humanized Antibodies" Immunology Today 14(6):243-246 (1993).
Excerpted translation of JP Patent Application Kokai Publication No. (JP-A) 2005-89354, published on Apr. 7, 2005.
Excerpted translation of JP Patent Application Kokai Publication No. (JP-A) 2003-310276, published on Nov. 5, 2003.

\* cited by examiner

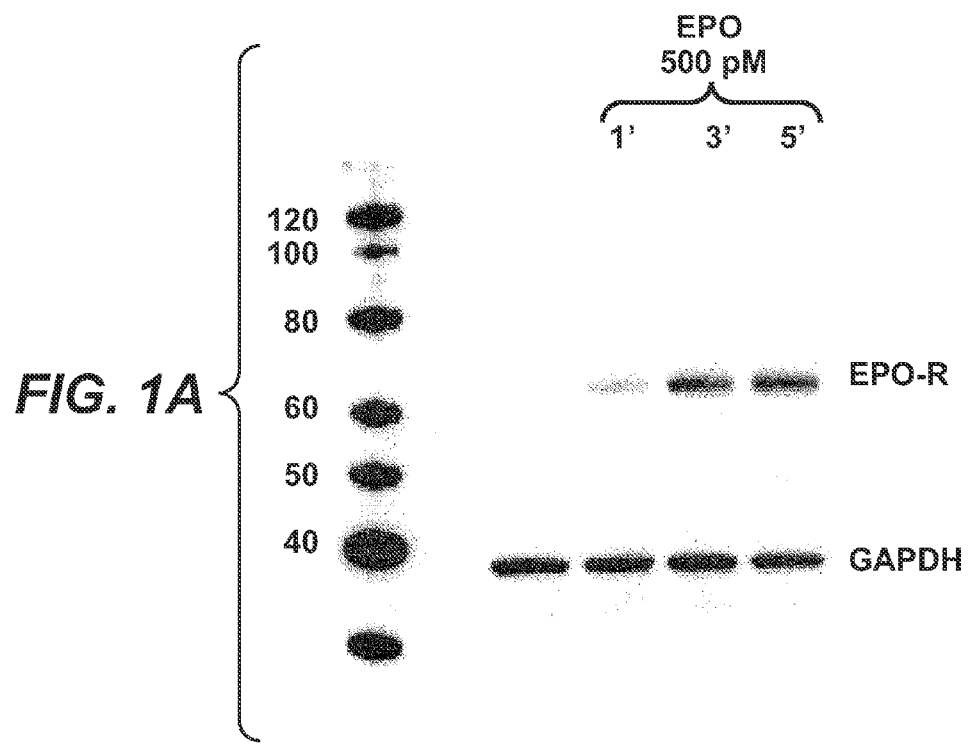
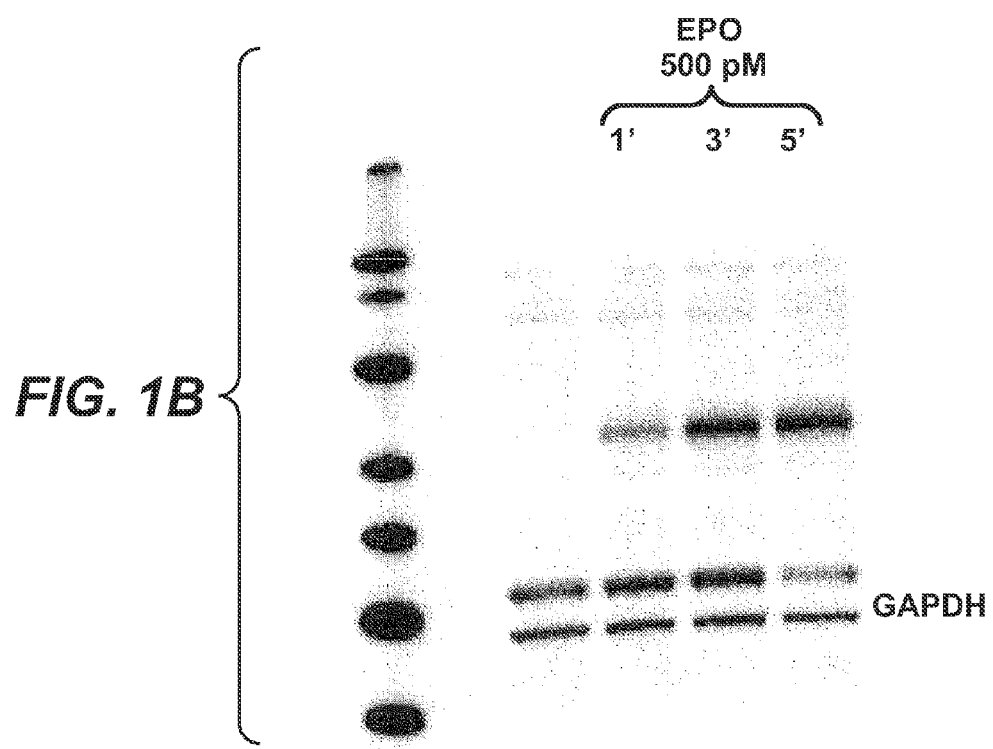

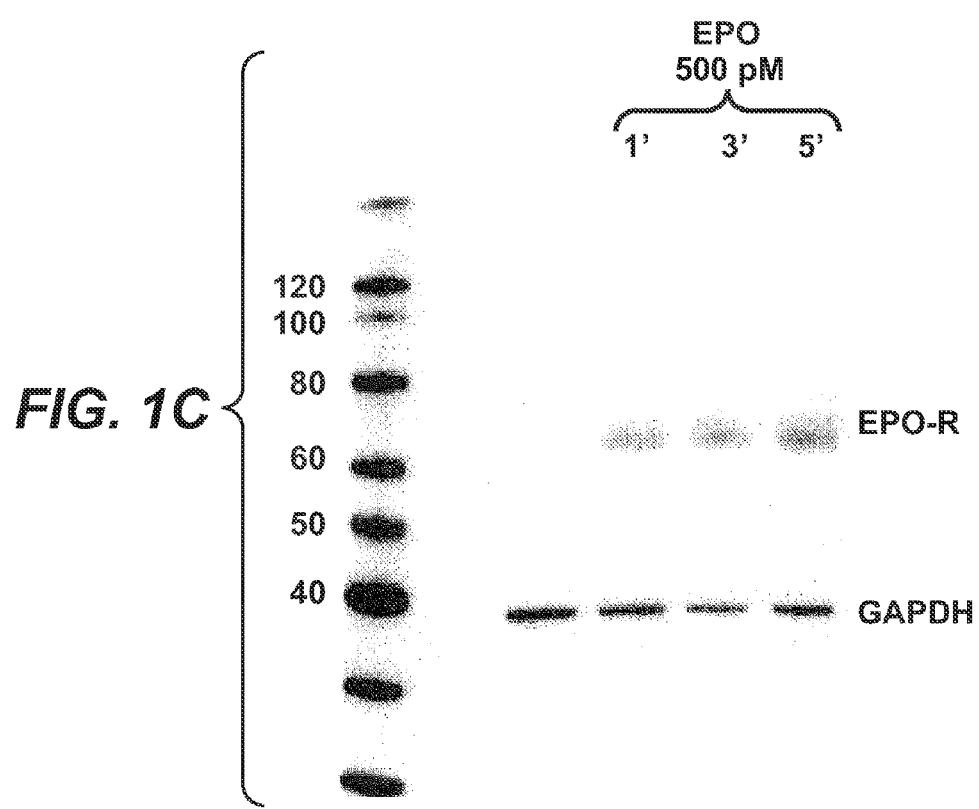

ANTIBODIES AGAINST HUMAN EPO RECEPTOR

CROSS REFERENCE TO RELATED APPLICATIONS

This application is a 371 of International Application No. PCT/EP2010/000130, filed 13 Jan. 2010, and claims the benefit of priority under 35 USC §119(a) to European patent application number 09000499.5, filed 15 Jan. 2009, the disclosures of which are incorporated herein by reference in their entirety.

BACKGROUND OF THE INVENTION

Human erythropoietin (EPO) is a 166-aa glycoprotein which is involved in the proliferation and differentiation of erythroid progenitor cells. These cellular responses are mediated by the human EPO receptor (EPO-R), a 508-aa glycoprotein. Human EPO receptor (EPO-R) is a protein of 508 amino acid length (Swiss Prot P19235) containing a single transmembrane domain and has been classified as a member of the growth hormone subfamily of class I cytokine receptors. EPO-R is e.g. described in Winkelmann, J. C. et al., Blood 76 (1990) 24-30 and Jones, S. S. et al., Blood 76 (1990) 31-35. Activation of EPO-R occurs by dimerization (Matthews, D. J., PNAS 93 (1996) 9471-9476). EPO-R comprises eight cytoplasmic tyrosine sites which become phosphorylated upon stimulation with EPO (Li, K. et al., J. Biol. Chem. 278 (2003) 40702-40709; Wu, H. et al., Proc. Natl. Acad. Sci. USA 94 (1997) 1806-1810) resulting in "activated EPO-R".

Antibodies against EPO-R are e.g. known from Andrea, A. D., Blood 82 (1993) 46-52; Elliott, S., Blood 107 (2006) 1892-1895; Kirkeby, A., J. Nerosci. 164 (2007) 50-58; Miura, 0., Arch. Biochem. 306 (1993) 200-208; and EP 1 146 056, EP 1 327 681, EP 0 773 962, EP 0 776 370, US 2002/0031806, US 2003/0215444, US 2004/0058393, US 2004/0071694, US 2004/0175379, US 2005/0227289, US 2005/0244409, US 2006/0018902, U.S. Pat. Nos. 6,998,124, 7,053,184, 7,081,523, WO 1995/005469, WO 1996/003438, WO 2000/061637, WO 2004/035603 A2, WO 2005/100403 A2. However it is known form the state of the art, that known antibodies against EPO-R are not able to discriminate between non activated and activated EPO-R (see Jelkmann, W. et al., Crit. Rev. One/Hematol. 67 (2008) 39-61; Li, K. et al., J. Biol. Chem. 278 (2003) 40702-40709, and Wu, H. et al., Proc. Natl. Acad. Sci. USA 94 (1997) 1806-1810).

SUMMARY OF THE INVENTION

The invention comprises an antibody specifically binding to activated human EPO receptor and discriminating between non activated and activated EPO-R, which allows specific analysis of the activation of EPO-R especially in cells and biopsies from human tissue.

The invention comprises an antibody, characterized in specifically binding human EPO receptor fragment TPPHLK YLYLVVSD (SEQ ID NO:25) comprising a phospho-tyrosyl residue at position 430 (underlined), GLSDGP YSNPYENSLIP (SEQ ID NO:26) comprising a phospho-tyrosyl residue at position 461 (underlined), or GLSDG-PYSNPYENSLIP (SEQ ID NO:26) comprising a phospho-tyrosyl residue at position 465 (underlined).

Numbering relates to EPO receptor amino acid sequence of UniProtKB/Swiss-Prot P19235 without signal peptide.

An antibody according to the invention does not bind EPO receptor fragment TPPHLKYLYLVVSD (SEQ ID NO:25) without a phospho-tyrosyl residue at position 430, GLSDG-PYSNPYENSLIP (SEQ ID NO:26) without a phospho-tyrosyl residue at position 461, or GLSDGPYSNPYENSLIP (SEQ ID NO:26) without a phospho-tyrosyl residue at position 465.

An antibody according to the invention specifically binds phosphorylated (activated) EPO receptor in lysates of UT7 cells which cells are expressing EPO-R in an amount of 100,000 to 500,000 receptors per cell (EPO-R expressing cells) and being treated with 500 pM EPO for activation. An antibody according to the invention does not bind EPO receptor in lysates of UT7 cells expressing EPO receptor and being not treated with EPO. Such binding can be measured by Western Blot.

Preferably the invention comprises an antibody binding to human EPO-R, characterized in comprising as heavy chain variable domain CDR3 region a CDR3 region of SEQ ID NO: 1, 9 or 17.

Preferably the antibody is characterized in that the heavy chain variable domain comprises CDR3 region of SEQ ID NO: 1, a CDR2 region of SEQ ID NO:2 and a CDR1 region of SEQ ID NO:3 or CDR3 region of SEQ ID NO:9, a CDR2 region of SEQ ID NO:10 and a CDR1 region of SEQ ID NO:11 or CDR3 region of SEQ ID NO:17, a CDR2 region of SEQ ID NO:18 and a CDR1 region of SEQ ID NO:19.

Preferably the antibody is characterized in that the heavy chain variable domain comprises a CDR3 region of SEQ ID NO: 1, a CDR2 region of SEQ ID NO:2 and a CDR1 region of SEQ ID NO:3 and in that the light chain variable domain comprises a CDR3 region of SEQ ID NO: 4, a CDR2 region of SEQ ID NO:5 and a CDR1 region of SEQ ID NO:6.

Preferably the antibody is characterized in that the heavy chain variable domain comprises a CDR3 region of SEQ ID NO: 9, a CDR2 region of SEQ ID NO:10 and a CDR1 region of SEQ ID NO:11 and in that the light chain variable domain comprises a CDR3 region of SEQ ID NO: 12, a CDR2 region of SEQ ID NO:13 and a CDR1 region of SEQ ID NO:14.

Preferably the antibody is characterized in that the heavy chain variable domain comprises a CDR3 region of SEQ ID NO: 17, a CDR2 region of SEQ ID NO:18 and a CDR1 region of SEQ ID NO:19 and in that the light chain variable domain comprises a CDR3 region of SEQ ID NO: 20, a CDR2 region of SEQ ID NO:21 and a CDR1 region of SEQ ID NO:22.

Preferably the antibody is characterized in that the heavy chain variable domain comprises SEQ ID NO:7, 15 or 23.

Preferably the antibody is characterized in that the light chain variable domain comprises SEQ ID NO:8, 16 or 24.

Preferably the antibody is characterized in that the heavy chain variable domain comprises SEQ ID NO:7 and the light chain variable domain comprises SEQ ID NO:8.

Preferably the antibody is characterized in that the heavy chain variable domain comprises SEQ ID NO:15 and the light chain variable domain comprises SEQ ID NO:16.

Preferably the antibody is characterized in that the heavy chain variable domain comprises SEQ ID NO:23 and the light chain variable domain comprises SEQ ID NO:24.

Preferably the antibody according to the invention is characterized in binding to EPO-R with a binding affinity of at least $10^{-8}$ M$^{-1}$ to $10^{-12}$ M$^{-1}$.

A further embodiment of the invention is a nucleic acid encoding a heavy chain and a light chain of an antibody according to the invention.

Human and other constant chains are well known in the state of the art and e.g. described by Kabat (see e.g. Johnson, G. and Wu, T. T., Nucleic Acids Res. 28 (2000) 214-218). It is further preferred that the antibody is of mouse origin and comprises the antibody variable sequence frame of a mouse antibody according to Kabat (see e.g. Johnson, G. and Wu, T. T., Nucleic Acids Res. 28 (2000) 214-218).

The antibody according to the invention is preferably of mouse, rabbit or human origin. As human antibody isotype IgG1 is preferred.

The invention further provides expression vectors containing nucleic acid according to the invention capable of expressing said nucleic acid in a prokaryotic or eukaryotic host cell, and host cells containing such vectors for the recombinant production of such an antibody.

The invention further comprises a prokaryotic or eukaryotic host cell comprising a vector according to the invention.

The invention further comprises a method for the production of a recombinant human or humanized antibody according to the invention, characterized by expressing a nucleic acid according to the invention in a prokaryotic or eukaryotic host cell and recovering said antibody from said cell or the cell culture supernatant. The invention further comprises the antibody obtainable by such a recombinant method.

The invention further comprises the use of an antibody according to the invention to determine/detect mammalian cells bearing/expressing activated EPO receptor.

Preferably an antibody according to the invention is used to determine activated EPO receptor in lysates of biopsies of human tissue samples. Preferably such detection is performed by Western Blot.

BRIEF DESCRIPTION OF THE FIGURES

FIGS. 1A, 1B and 1C: Time dependent phosphorylation of human EPOR in UT-7_EPOR cells. Western blot analysis of lysates of UT7-EPOR cells stained with the different monoclonal antibodies directed against phosphorylated human EPOR. FIG. 1A: pY430 (C1.16.7.5), FIG. 1B: pY461 (C1.8.7.16), FIG. 1C: pY465 (C1.24.11.31). All monoclonal antibodies specifically detect EPOR only when cells are stimulated with EPO, unstimulated cells (−) are not labeled by the antibodies. GAPDH (Glyceraldehyde 3-phosphate dehydrogenase) was used as loading control.

DETAILED DESCRIPTION OF THE INVENTION

The term "antibody" encompasses the various forms of antibody structures including but not being limited to whole antibodies and antibody fragments.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Houston, J. S., Methods Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to EPO-R, namely being able to assemble together with a $V_H$ domain to a functional antigen binding site and thereby providing an antibody with the properties of specifically binding to human EPO-R.

The term "humanized antibody" refers to antibodies in which the framework and/or "complementarity determining regions" (CDR) have been modified to comprise the CDR of an immunoglobulin of different species as compared to that of the parent immunoglobulin. In a preferred embodiment, a mouse CDR is grafted into the framework region of a human antibody to prepare the "humanized antibody". See, e.g., Riechmann, L. et al., Nature 332 (1988) 323-327; and Neuberger, M. S. et al., Nature 314 (1985) 268-270.

The term "comprises a heavy chain CDR3 region of SEQ ID NO:1" denotes that the antibody comprises as sequence of its heavy chain CDR3 region the amino acid sequence of SEQ ID NO:1. The same denotes for the other five CDR regions of the antibody.

The term "binding to activated EPO-R" as used herein means binding of the antibody to human activated EPO-R in a biochemical binding assay measured by Western Blotting. Binding is found if the antibody causes an S/N (signal/noise) ratio of 400 or more at an antibody concentration of 1 µg/ml. The term "not binding to EPO-R" as used herein means binding of the antibody to human EPO-R in a biochemical binding assay measured by Western Blotting. No binding is found if the antibody causes an S/N (signal/noise) ratio of lower than 400 at an antibody concentration of 1 µg/ml. Binding of the antibodies according to the invention to non activated EPO R is not detectable in Western Blots, therefore the S/N ratio is even lower than 10 and preferably about 1 or lower.

The term "binding of EPO to EPO receptor" as used herein means binding of the EPO to human activated EPO-R in a biochemical binding assay measured by Western Blotting. No binding is found if EPO causes an S/N (signal/noise) ratio of no more than 10 at an EPO concentration of 1 µg/ml.

The term "pY430" as used herein means a 17 amino-acid synthetic peptide corresponding to residues 424-437 of the mature human erythropoietin receptor (TPPHLKYLYLV-VSD, SEQ ID NO:25), comprising a phospho-tyrosyl residue at position 430. The term "pY461" as used herein means a 17 amino-acid synthetic peptide corresponding to residues 455-471 of the mature human erythropoietin receptor (GLSDG-PYSNPYENSLIP, SEQ ID NO:26), comprising a phospho-tyrosyl residue at position 461. The term "pY465" as used herein means a 17 amino-acid synthetic peptide corresponding to residues 455-471 of the mature human erythropoietin receptor (GLSDGPYSNPYENSLIP, SEQ ID NO:26), comprising a phospho-tyrosyl residue at position 465.

The antibody according to the invention is characterized in specifically binding pY430, pY461 or pY465 in ELISA at a S/N ratio of 10 or more at an antibody concentration of 0.1 µg/ml.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refers to the amino acid residues of an antibody which are responsible for antigen-binding. The antigen-binding portion of an antibody comprises amino acid residues from the "complementarity determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are collinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice.

As used herein, the expressions "cell", "cell line", and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

Examples of useful human heavy chain constant region comprises an amino acid of SEQ ID NO: 23. For example an useful human light chain constant region comprises an amino acid sequence of a kappa-light chain constant region of SEQ ID NO: 24.

The invention comprises a method for detecting or determination of activated EPO-R in human cells tissues, and biopsies.

The invention comprises the use of an antibody according to the invention for diagnosis of activated EPO-R in human cells tissues, and biopsies.

The invention comprises the use of an antibody according to the invention for the preparation of a diagnostics assay for detecting or determining activated EPO-R in human cells tissues, and biopsies.

The antibodies according to the invention include, in addition, such antibodies having "conservative sequence modifications" (variant antibodies), nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, a predicted nonessential amino acid residue in a human anti-EPO-R antibody can be preferably replaced with another amino acid residue from the same side chain family. A "variant" anti-EPO-R antibody, refers therefore herein to a molecule which differs in amino acid sequence from a "parent" anti-EPO-R antibody amino acid sequence by up to ten, preferably from about two to about five, additions, deletions and/or substitutions in one or more variable region of the parent antibody. Amino acid substitutions can be performed by mutagenesis based upon molecular modeling as described by Riechmann, L. et al., Nature 332 (1988) 323-327 and Queen, C. et al., Proc. Natl. Acad. Sci. USA 86 (1989) 10029-10033.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NSO cells, SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S. C., Protein Expr. Purif. 17 (1999) 183-202; Geisse, S. et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Expression in NSO cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86

(1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Amino acid sequence variants of human EPO-R antibody are prepared by introducing appropriate nucleotide changes into the antibody encoding DNA, or by peptide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability, or facilitate the purification.

Any cysteine residue not involved in maintaining the proper conformation of the anti-EPO-R antibody may also be substituted, generally with serine, to improve the oxidative stability of the molecule and to prevent aberrant crosslinking. Conversely, cysteine bond(s) may be added to the antibody to improve its stability (particularly where the antibody is an antibody fragment such as an Fv fragment).

Nucleic acid molecules encoding amino acid sequence variants of anti-EPO-R antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-EPO-R antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a diagnostic composition, e.g. for the determination of activated EPO-R in human cells tissues, and biopsies.

Description of the Sequences

| | |
|---|---|
| SEQ ID NO: 1 | heavy chain CDR3, Mab Cl.16.7.5 |
| SEQ ID NO: 2 | heavy chain CDR2, Mab Cl.16.7.5 |
| SEQ ID NO: 3 | heavy chain CDR1, Mab Cl.16.7.5 |
| SEQ ID NO: 4 | light chain CDR3, Mab Cl.16.7.5 |
| SEQ ID NO: 5 | light chain CDR2, Mab Cl.16.7.5 |
| SEQ ID NO: 6 | light chain CDR1, Mab Cl.16.7.5 |
| SEQ ID NO: 7 | heavy chain variable domain, Mab Cl.16.7.5 |
| SEQ ID NO: 8 | light chain variable domain, Mab Cl.16.7.5 |

-continued

| | |
|---|---|
| SEQ ID NO: 9 | heavy chain CDR3, Mab Cl.8.7.16 |
| SEQ ID NO: 10 | heavy chain CDR2, Mab Cl.8.7.16 |
| SEQ ID NO: 11 | heavy chain CDR1, Mab Cl.8.7.16 |
| SEQ ID NO: 12 | light chain CDR3, Mab Cl.8.7.16 |
| SEQ ID NO: 13 | light chain CDR2, Mab Cl.8.7.16 |
| SEQ ID NO: 14 | light chain CDR1, Mab Cl.8.7.16 |
| SEQ ID NO: 15 | heavy chain variable domain, Mab Cl.8.7.16 |
| SEQ ID NO: 16 | light chain variable domain, Mab Cl.8.7.16 |
| SEQ ID NO: 17 | heavy chain CDR3, Mab Cl.24.11.31 |
| SEQ ID NO: 18 | heavy chain CDR2, Mab Cl.24.11.31 |
| SEQ ID NO: 19 | heavy chain CDR1, Mab Cl.24.11.31 |
| SEQ ID NO: 20 | light chain CDR3, Mab Cl.24.11.31 |
| SEQ ID NO: 21 | light chain CDR2, Mab Cl.24.11.31 |
| SEQ ID NO: 22 | light chain CDR1, Mab Cl.24.11.31 |
| SEQ ID NO: 23 | heavy chain variable domain, Mab Cl.24.11.31 |
| SEQ ID NO: 24 | light chain variable domain, Mab Cl.24.11.31 |
| SEQ ID NO: 25 | synthetic peptide |
| SEQ ID NO: 26 | synthetic peptide |

EXAMPLE 1

Generation of Phospho-Specific EPOR Monoclonal Antibodies pY430 (C1.16.7.5): a 17 amino-acid synthetic peptide corresponding to residues 424-437 of the mature human erythropoietin receptor (TPPHLKYLYLVVSD, SEQ ID NO:25), comprising a phospho-tyrosyl residue at position 430 was used as immunogen.

pY461 (C1.8.7.16): a 17 amino-acid synthetic peptide corresponding to residues 455-471 of the mature human erythropoietin receptor (GLSDGPYSNPYENSLIP, SEQ ID NO:26), comprising a phospho-tyrosyl residue at position 461 was used as immunogen.

pY465 (C1.24.11.31): a 17 amino-acid synthetic peptide corresponding to residues 455-471 of the mature human erythropoietin receptor (GLSDGPYSNPYENSLIP, SEQ ID NO:26), comprising a phospho-tyrosyl residue at position 465 was used as immunogen.

For immunization the peptides were coupled to KLH via a C terminal cystein. Balb/c mice were immunized with immunogen every four weeks for 3 times followed by an i.v. boost on day 4 before fusion, splenocytes were harvested, and fused with Ag8 myeloma cells. Screening for phospho-specific antibodies was done by differential testing on phospho-vs. non-phospho-form of the peptide (which otherwise was identical to the phospho-peptide) using peptide coated ELISA microtiter plates following standard procedures. Antibody clones were selected because they detected one specific band corresponding to the EPOR on Western Blots of cell lysates that have been stimulated with EPO (example 2).

SDS-PAGE and Western Blotting:

The SDS-PAGE and Western blotting were performed according to standard procedures and the Nupage® gel system of Invitrogen. The lysates corresponding to $5 \cdot 10^4$-$10^5$ cells were loaded in each line of a Nupage® Novex 4-12% Bis-Tris gel. The proteins were then transferred onto PVDF (Polyvinylidene Fluoride) membranes and incubated with the antibodies and anti-GAPDH antibody (Abcam m9484, Abcam plc UK)) for 2 hours at room temperature or overnight at 4° C. After washing, the membranes were incubated with a conjugate anti-mouse IgG-POD and developed using ECL reagents (Lumi-Light$^{PLUS}$ Western blotting substrate, Roche Applied Science #2015218).

Antibodies C1.24.11.31, C1.16.7.5 and C1.8.7.16 were selected as binding specifically to activated EPO receptor only without binding to non-activated EPO receptor (FIG. 1A, FIG. 1B and FIG. 1C).

EXAMPLE 2

Activation of UT-7 Cells

UT-7 cell line is a human factor-dependent erythroleukemia cell line (Human bone marrow acute myeloid leukemia cell line DSMZ: ACC 137), requiring EPO for long-term growth. UT7 cells were maintained in RPMI medium comprising in addition L-glutamine (2 mM), non-essential amino acids (1×), and sodium pyruvate (1 mM) (starvation medium), supplemented with 10% fetal calf serum and 10 U/ml GM-CSF. Transduced cells (UT7/EPOR) were maintained in the same medium as untransduced (25 U/ml GM-CSF instead of 10 U/ml) with the addition of 0.4 mg/ml zeocine. Before each stimulation the cells were starved by incubation overnight in RPMI media supplemented with L-glutamine (2 mM), non-essential amino acids (1×), sodium pyruvate (1 mM) and 0.1% fetal calf serum.

Transduction:

UT-7 cells were transduced with the supernatant from GP2-293 (Clontech Laboratories, Inc) cells transiently transfected with a retroviral expression vector encoding hEPOR and pVSV-G (an expression vector encoding the G glycoprotein of the rhabdovirus vesicular stomatitis virus). Two days after transduction the medium was replaced with fresh supplemented RPMI containing 0.4 mg/ml zeocine and 25 U/ml GM-CSF. After selection a cell line of UT-7 cells stable expressing EPOR on their surface was obtained.

Stimulation:

Serum starved cells were stimulated for the times indicated with 500 pM erythropoietin in starvation medium (supplemented with 0.1% fetal calf serum) at 37° C. for 1, 3 and 5 minutes. After stimulation the cells were centrifuged, the medium was discarded and the pellet was incubated in ice-cold lysis buffer [Tris 20 mM (pH7.4), NaCl 137 mM, Glycerol 10%, Nonidet® P-40 1%, protease inhibitors 1× (Pierce, #78410), phosphatase inhibitors 1× (Pierce #78420)] for 30 minutes at 4° C. followed by centrifugation at 13000 rpm for 10 minutes at 4° C. The lysate supernatant was boiled in sample buffer (Nupage®, Invitrogen) in the presence of a reducing agent and either directly used for SDS-PAGE.

Specific binding of the Mabs was tested by ELISA on microtiterplates coated with the corresponding biotinylated peptide according to standard procedures as described in example 1. Already within 1 min a clear activation of human EPOR can be demonstrated while un-stimulated cells do not show any detectable basal level of activation.

EXAMPLE 3

Western Blot Assay for Binding of Mabs to UT-7/EPOR Cells Activated by EPO

UT7/EPOR cells were stimulated as described above and analyzed by Western Blot. On Western blot the Mabs recognize one band at MW 66 kD corresponding to the EPOR (FIG. 1A, FIG. 1B and FIG. 1C) in cells that are stimulated with 0.5 nM EPO for 1-5 min. Already within 1 min a clear activation of human EPOR can be demonstrated while un-stimulated cells do not show any detectable basal level of activation (FIG. 1A, FIG. 1B and FIG. 1C). As loading control GAPDH was used. Thus, these antibodies specifically analyze the activation of EPOR by ESAs (erythropoietin stimulating agents).

The invention claimed is:

1. An antibody that binds to human erythropoietin (EPO) receptor, wherein said antibody comprises a heavy chain CDR3 region of SEQ ID NO:17, a heavy chain CDR2 region of SEQ ID NO:18, a heavy chain CDR1 region of SEQ ID NO:19, a light chain CDR3 region of SEQ ID NO:20, a light chain CDR2 region of SEQ ID NO:21, and a light chain CDR1 region of SEQ ID NO:22.

2. The antibody according to claim 1, wherein said antibody comprises a heavy chain variable domain comprising SEQ ID NO:23 and a light chain variable domain comprising SEQ ID NO:24.

3. A nucleic acid encoding the antibody according to claim 1.

4. A nucleic acid encoding the antibody according to claim 2.

5. A diagnostic kit comprising the antibody according to claim 1 or 2.

6. An expression vector comprising the nucleic acid according to claim 3 or 4.

7. A prokaryotic or eukaryotic host cell comprising the expression vector according to claim 6.

8. A method for the production of an antibody comprising expressing the nucleic acid according to claim 3 or 4 in a prokaryotic or eukaryotic host cell and recovering said antibody from said cell or the cell culture supernatant.

9. A method for detecting activated EPO receptor in human cells, tissues, or biopsies comprising contacting an antibody according to claim 1 or 2 with said human cells, tissues or biopsies.

10. The method according to claim 9, wherein said sample is a lysate of human tissue.

11. The method according to claim 10, wherein said detecting is performed by Western Blot or ELISA.

* * * * *

SEQUENCE LISTING

```
<160> NUMBER OF SEQ ID NOS: 26

<210> SEQ ID NO 1
<211> LENGTH: 9
<212> TYPE: PRT
<213> ORGANISM: Mus musculus

<400> SEQUENCE: 1

Gly Pro His Tyr Tyr Gly Ser Ser Tyr
1               5

<210> SEQ ID NO 2
<211> LENGTH: 17
<212> TYPE: PRT
<213> ORGANISM: Mus musculus

<400> SEQUENCE: 2

Glu Ile Asn Pro Asp Ser Ser Val Ile Asn Tyr Thr Pro Ser Leu Lys
1               5                   10                  15

Asp

<210> SEQ ID NO 3
<211> LENGTH: 10
<212> TYPE: PRT
<213> ORGANISM: Mus musculus

<400> SEQUENCE: 3

Gly Phe Asp Phe Ser Arg His Trp Val Asn
```

<210> SEQ ID NO 4
<211> LENGTH: 9
<212> TYPE: PRT
<213> ORGANISM: Mus musculus

<400> SEQUENCE: 4

Gln Gln Arg Ser Ser Tyr Pro Tyr Thr
1               5

<210> SEQ ID NO 5
<211> LENGTH: 7
<212> TYPE: PRT
<213> ORGANISM: Mus musculus

<400> SEQUENCE: 5

Thr Thr Ser Asn Leu Ala Ser
1               5

<210> SEQ ID NO 6
<211> LENGTH: 10
<212> TYPE: PRT
<213> ORGANISM: Mus musculus

<400> SEQUENCE: 6

Ser Ala Ser Ser Ser Val Gly Phe Met His
1               5                   10

<210> SEQ ID NO 7
<211> LENGTH: 118
<212> TYPE: PRT
<213> ORGANISM: Mus musculus

<400> SEQUENCE: 7

Glu Val Lys Leu Leu Glu Ser Gly Gly Gly Leu Val Gln Pro Gly Gly
1               5                   10                  15

Ser Leu Lys Leu Ser Cys Ser Ala Ser Gly Phe Asp Phe Ser Arg His
                20                  25                  30

Trp Val Asn Trp Val Arg Gln Ala Pro Gly Lys Gly Leu Glu Trp Ile
            35                  40                  45

Gly Glu Ile Asn Pro Asp Ser Ser Val Ile Asn Tyr Thr Pro Ser Leu
        50                  55                  60

Lys Asp Lys Phe Ile Ile Ser Arg Asp Asn Ala Lys Asn Ser Leu Tyr
65                  70                  75                  80

Leu Gln Met Gly Lys Val Ser Ser Glu Asp Thr Ala Leu Tyr Tyr Cys
                85                  90                  95

Val Arg Gly Pro His Tyr Tyr Gly Ser Ser Tyr Trp Gly Arg Gly Thr
            100                 105                 110

Leu Val Thr Val Ser Ala
        115

<210> SEQ ID NO 8
<211> LENGTH: 106
<212> TYPE: PRT
<213> ORGANISM: Mus musculus

<400> SEQUENCE: 8

Gln Val Val Leu Thr Gln Ser Pro Ala Ile Met Ser Ala Ser Pro Gly
1               5                   10                  15

Glu Lys Val Thr Met Thr Cys Ser Ala Ser Ser Ser Val Gly Phe Met

```
                    20                  25                  30
His Trp Phe Gln Gln Lys Pro Gly Thr Ser Pro Lys Leu Trp Ile Tyr
                35                  40                  45
Thr Thr Ser Asn Leu Ala Ser Gly Val Pro Thr Arg Phe Ser Gly Ser
            50                  55                  60
Gly Ser Gly Thr Ser Tyr Ser Leu Thr Ile Ser Arg Met Glu Ala Asp
65                  70                  75                  80
Asp Ala Ala Thr Tyr Tyr Cys Gln Gln Arg Ser Ser Tyr Pro Tyr Thr
                85                  90                  95
Phe Gly Gly Gly Thr Asn Leu Glu Ile Lys
            100                 105

<210> SEQ ID NO 9
<211> LENGTH: 10
<212> TYPE: PRT
<213> ORGANISM: Mus musculus

<400> SEQUENCE: 9

Arg Gly Phe Asn Tyr Gly Gly Phe Ala Tyr
1               5                   10

<210> SEQ ID NO 10
<211> LENGTH: 19
<212> TYPE: PRT
<213> ORGANISM: Mus musculus

<400> SEQUENCE: 10

His Val Arg Asn Arg Thr Asn Tyr Tyr Ala Thr Ser Tyr Gly Ala Ser
1               5                   10                  15

Val Lys Asp

<210> SEQ ID NO 11
<211> LENGTH: 14
<212> TYPE: PRT
<213> ORGANISM: Mus musculus

<400> SEQUENCE: 11

Cys Ala Ala Ser Gly Phe Thr Phe Ser Phe Tyr Gly Met Asn
1               5                   10

<210> SEQ ID NO 12
<211> LENGTH: 9
<212> TYPE: PRT
<213> ORGANISM: Mus musculus

<400> SEQUENCE: 12

His Gln Tyr Phe Ser Tyr Pro Trp Thr
1               5

<210> SEQ ID NO 13
<211> LENGTH: 7
<212> TYPE: PRT
<213> ORGANISM: Mus musculus

<400> SEQUENCE: 13

Trp Ala Ser Thr Arg Glu Ser
1               5

<210> SEQ ID NO 14
<211> LENGTH: 17
<212> TYPE: PRT
```

```
<400> SEQUENCE: 14

Lys Ser Ser Gln Ser Leu Leu Tyr Ser Asn Asn Gln Lys Asn Tyr Leu
1               5                   10                  15

Ala

<210> SEQ ID NO 15
<211> LENGTH: 121
<212> TYPE: PRT
<213> ORGANISM: Mus musculus

<400> SEQUENCE: 15

Glu Val Gln Leu Val Glu Ser Gly Gly Gly Leu Val Gln Pro Glu Gly
1               5                   10                  15

Ser Leu Lys Leu Ser Cys Ala Ala Ser Gly Phe Thr Phe Ser Phe Tyr
            20                  25                  30

Gly Met Asn Trp Val Arg Gln Ala Pro Gly Lys Gly Leu Glu Trp Val
        35                  40                  45

Ala His Val Arg Asn Arg Thr Asn Tyr Ala Thr Ser Tyr Gly Ala
    50                  55                  60

Ser Val Lys Asp Arg Phe Thr Ile Ser Arg Asp Asp Ser Gln Ser Leu
65                  70                  75                  80

Val Tyr Leu Leu Met Asn Asn Leu Lys Thr Glu Asp Thr Ala Met Tyr
                85                  90                  95

Tyr Cys Val Arg Arg Gly Phe Asn Tyr Gly Gly Phe Ala Tyr Trp Gly
            100                 105                 110

Gln Gly Thr Leu Val Thr Val Ser Ala
        115                 120

<210> SEQ ID NO 16
<211> LENGTH: 113
<212> TYPE: PRT
<213> ORGANISM: Mus musculus

<400> SEQUENCE: 16

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Val Phe Ala Leu Thr
65                  70                  75                  80

Ile Ser Ser Val Lys Ala Glu Asp Leu Ala Val Tyr Tyr Cys His Gln
                85                  90                  95

Tyr Phe Ser Tyr Pro Trp Thr Phe Gly Gly Gly Thr Lys Leu Glu Ile
            100                 105                 110

Lys

<210> SEQ ID NO 17
<211> LENGTH: 14
<212> TYPE: PRT
<213> ORGANISM: Mus musculus

<400> SEQUENCE: 17
```

His Gly Gly Tyr Gln Gly Ile Ser Arg Tyr Ala Met Asp Tyr
1               5                   10

<210> SEQ ID NO 18
<211> LENGTH: 19
<212> TYPE: PRT
<213> ORGANISM: Mus musculus

<400> SEQUENCE: 18

Arg Ile Arg Thr Asn Asn Asn Tyr Glu Val Tyr Tyr Ala Asp Ser
1               5                   10                  15

Val Lys Asp

<210> SEQ ID NO 19
<211> LENGTH: 10
<212> TYPE: PRT
<213> ORGANISM: Mus musculus

<400> SEQUENCE: 19

Gly Phe Thr Phe Asn Thr Tyr Ala Met Asn
1               5                   10

<210> SEQ ID NO 20
<211> LENGTH: 9
<212> TYPE: PRT
<213> ORGANISM: Mus musculus

<400> SEQUENCE: 20

Ser Gln Asn Thr His Val Pro Phe Thr
1               5

<210> SEQ ID NO 21
<211> LENGTH: 7
<212> TYPE: PRT
<213> ORGANISM: Mus musculus

<400> SEQUENCE: 21

Lys Val Ser Asn Arg Leu Ser
1               5

<210> SEQ ID NO 22
<211> LENGTH: 16
<212> TYPE: PRT
<213> ORGANISM: Mus musculus

<400> SEQUENCE: 22

Arg Ser Ser Gln Ser Leu Val His Asp Asn Gly Asn Thr Tyr Phe His
1               5                   10                  15

<210> SEQ ID NO 23
<211> LENGTH: 125
<212> TYPE: PRT
<213> ORGANISM: Mus musculus

<400> SEQUENCE: 23

Glu Val Gln Leu Val Glu Ser Gly Gly Gly Leu Val Arg Pro Gln Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Ile
            35                  40                  45

Ala Arg Ile Arg Thr Asn Asn Asn Tyr Glu Val Tyr Tyr Ala Asp
        50                  55                  60

```
Ser Val Lys Asp Arg Phe Thr Ile Ser Arg Asp Asp Ser Glu Ser Met
 65                  70                  75                  80

Leu Tyr Leu Gln Met Asn Asn Leu Lys Thr Glu Asp Thr Ala Met Tyr
                 85                  90                  95

Tyr Cys Val Arg His Gly Gly Tyr Gln Gly Ile Ser Arg Tyr Ala Met
            100                 105                 110

Asp Tyr Trp Gly Gln Gly Thr Ser Val Thr Val Ser Ser
            115                 120                 125

<210> SEQ ID NO 24
<211> LENGTH: 112
<212> TYPE: PRT
<213> ORGANISM: Mus musculus

<400> SEQUENCE: 24

Asp Phe Val Leu Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Asp
             20                  25                  30

Asn Gly Asn Thr Tyr Phe His Trp Phe Leu Gln Lys Pro Gly Gln Ser
         35                  40                  45

Pro Lys Leu Leu Ile Tyr Lys Val Ser Asn Arg Leu Ser Gly Val Pro
     50                  55                  60

Asp Arg Phe Ser Gly Ser Gly Ser Ala Thr Asp Phe Thr Leu Lys Ile
 65                  70                  75                  80

Ser Arg Val Glu Ala Glu Asp Leu Gly Val Tyr Phe Cys Ser Gln Asn
                 85                  90                  95

Thr His Val Pro Phe Thr Phe Gly Ser Gly Thr Arg Leu Glu Met Lys
            100                 105                 110

<210> SEQ ID NO 25
<211> LENGTH: 14
<212> TYPE: PRT
<213> ORGANISM: Homo sapiens

<400> SEQUENCE: 25

Thr Pro Pro His Leu Lys Tyr Leu Tyr Leu Val Val Ser Asp
 1               5                  10

<210> SEQ ID NO 26
<211> LENGTH: 17
<212> TYPE: PRT
<213> ORGANISM: Homo sapiens

<400> SEQUENCE: 26

Gly Leu Ser Asp Gly Pro Tyr Ser Asn Pro Tyr Glu Asn Ser Leu Ile
 1               5                  10                  15

Pro
```